(12) United States Patent
Rowlandson et al.

(10) Patent No.: US 8,060,192 B2
(45) Date of Patent: Nov. 15, 2011

(54) METHOD AND SYSTEM FOR DETECTING T-WAVE ALTERNANS

(75) Inventors: Gordon Ian Rowlandson, Milwaukee, WI (US); Willi Kaiser, Emmendingen (DE); Michael Slawnych, Calgary (CA); Joel Qiuzhen Xue, Germantown, WI (US); Derek Exner, Calgary (CA)

(73) Assignee: General Electric Company, Schenectady, NY (US)

( * ) Notice: Subject to any disclaimer, the term of this patent is extended or adjusted under 35 U.S.C. 154(b) by 326 days.

(21) Appl. No.: 12/332,095

(22) Filed: Dec. 10, 2008

(65) Prior Publication Data

US 2010/0145207 A1 Jun. 10, 2010

(51) Int. Cl.
*A61B 5/0402* (2006.01)
(52) U.S. Cl. ...................................................... 600/515
(58) Field of Classification Search ........... 600/115–119
See application file for complete search history.

(56) References Cited

U.S. PATENT DOCUMENTS

| | | | |
|---|---|---|---|
| 5,570,696 A | 11/1996 | Arnold et al. | |
| 5,704,365 A | 1/1998 | Albrecht et al. | |
| 5,713,367 A | 2/1998 | Arnold et al. | |
| 5,891,045 A | 4/1999 | Albrecht et al. | |
| 5,935,082 A | 8/1999 | Albrecht et al. | |
| 6,169,919 B1 | 1/2001 | Nearing et al. | |
| 6,453,191 B2 | 9/2002 | Krishnamachari | |
| 6,668,189 B2 | 12/2003 | Kaiser et al. | |
| 6,735,466 B1 | 5/2004 | Haghighi-Mood | |
| 6,823,213 B1* | 11/2004 | Norris et al. | 607/9 |
| 7,027,857 B2 | 4/2006 | Kaiser et al. | |
| 7,050,846 B2* | 5/2006 | Sweeney et al. | 600/515 |
| 7,221,976 B2* | 5/2007 | Couderc et al. | 600/515 |
| 2006/0116596 A1* | 6/2006 | Zhou et al. | 600/516 |
| 2009/0192398 A1* | 7/2009 | Zhou et al. | 600/517 |

* cited by examiner

*Primary Examiner* — Carl H Layno
*Assistant Examiner* — Paula J Stice
(74) *Attorney, Agent, or Firm* — Andrus, Sceales, Starke & Sawall, LLP

(57) ABSTRACT

A method for generating a cardiac electrical instability assessment is disclosed herein. The method includes obtaining a short duration T-wave alternans (SDTWA) measurement, obtaining a long duration T-wave alternans (LDTWA) measurement, and obtaining a cardiac electrical instability assessment based on both the SDTWA measurement and the LDTWA measurement.

21 Claims, 4 Drawing Sheets

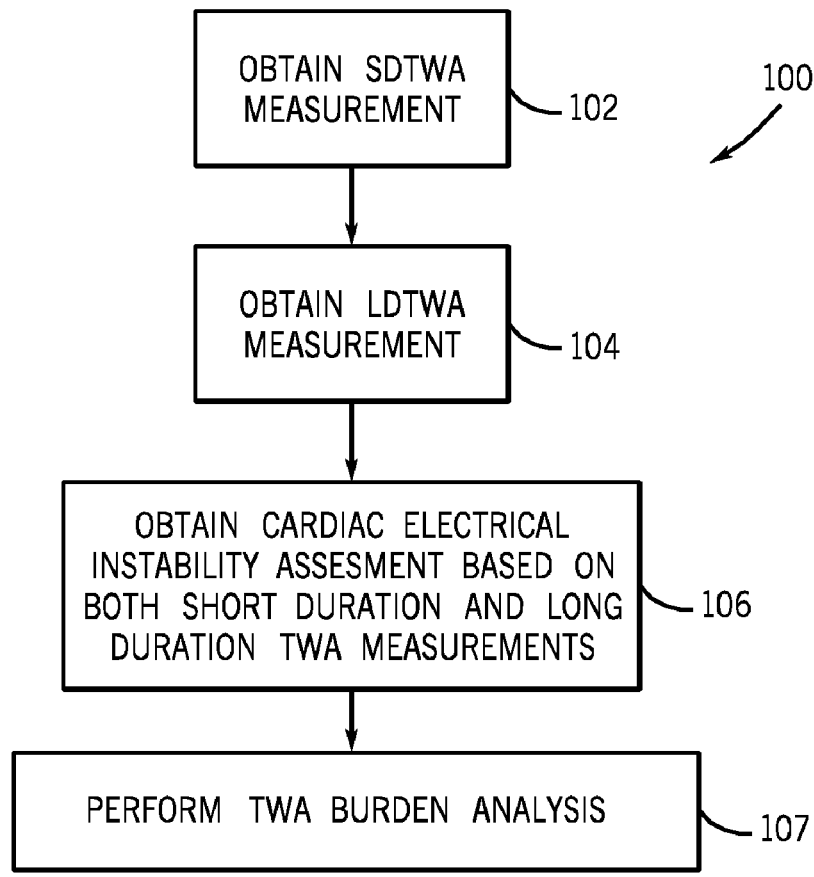
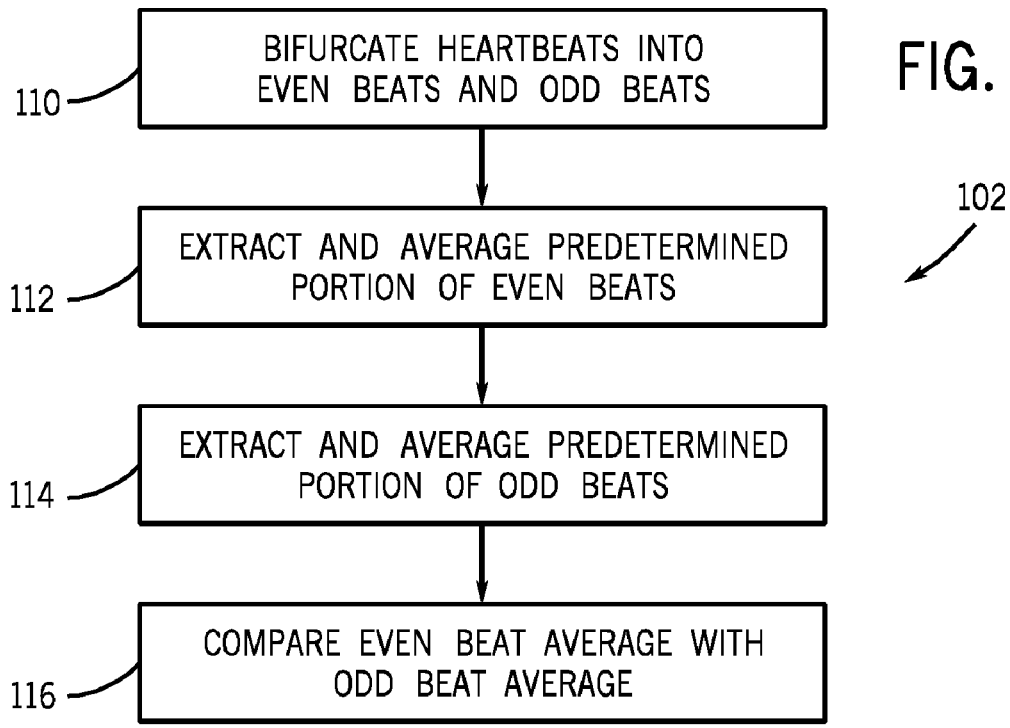

METHOD AND SYSTEM FOR DETECTING T-WAVE ALTERNANS

BACKGROUND OF THE INVENTION

This disclosure relates to method and system for detecting T-wave alternans.

An electrocardiogram (ECG) of a single heartbeat is commonly referred to as a PQRST complex. The PQRST complex includes a P-wave that corresponds to activity in the atria, a QRS complex that represents the electrical activation of the ventricles, and a T-wave that represents the electrical recovery or recharge phase of the ventricles. The PQRST complex also includes an ST segment connecting the QRS complex and the T-wave. T-wave alternans (TWA) is an electrophysiological phenomenon that is evident in the ECG as an alternating pattern of ST segment and/or T-wave morphologies on successive beats.

Clinical studies have demonstrated that TWA is an indicator of cardiac electrical instability. One problem is that it is difficult to identify and measure the specific TWA morphological patterns that are most indicative of cardiac electrical instability.

SUMMARY OF THE INVENTION

The above-mentioned shortcomings, disadvantages and problems are addressed herein which will be understood by reading and understanding the following specification.

In an embodiment, a method includes obtaining a short duration T-wave alternans (TWA) measurement, obtaining a long duration TWA measurement, and obtaining a cardiac electrical instability assessment based on both the short duration TWA measurement and the long duration TWA measurement.

In another embodiment, a method includes obtaining a short duration TWA differential measurement, and obtaining a long duration TWA differential measurement. The method also includes eliminating any data exceeding a first high differential limit from the long duration TWA measurement. Cardiac electrical instability is diagnosed if the short duration TWA differential measurement exceeds a second high differential limit or if the long duration TWA differential measurement exceeds a low differential limit. The method also includes performing a TWA burden analysis in order to obtain a degree of concern assessment.

In yet another embodiment, a system includes a plurality of sensors; and a processor operatively connected to the plurality of sensors. The processor is configured to generate a cardiac electrical instability assessment based on a short duration TWA measurement and a long duration TWA measurement.

Various other features, objects, and advantages of the invention will be made apparent to those skilled in the art from the accompanying drawings and detailed description thereof.

BRIEF DESCRIPTION OF THE DRAWINGS

FIG. 4 is a flow chart in accordance with an embodiment;

FIG. 5 is a flow chart in accordance with an embodiment;

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
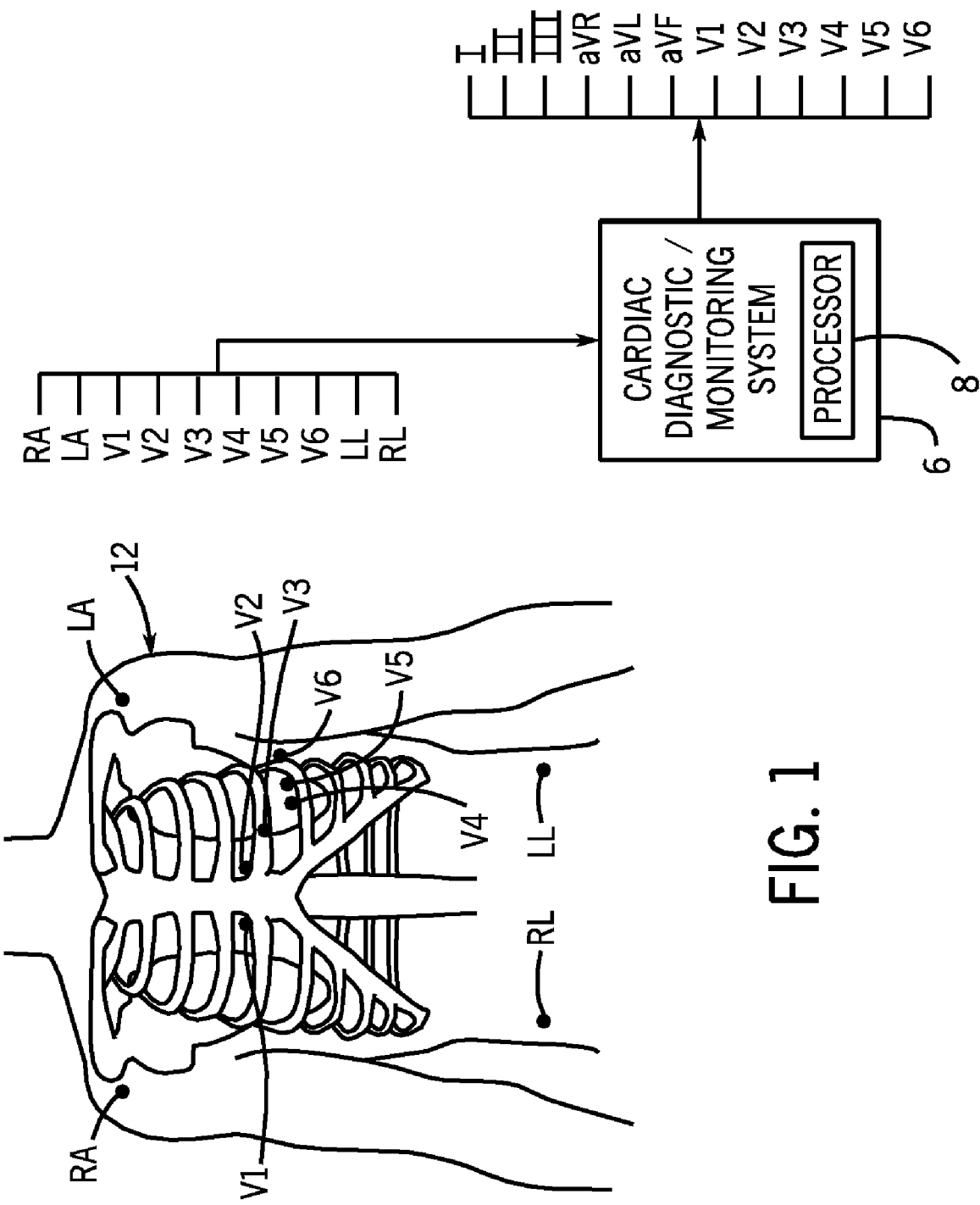
FIG. 1 is a schematic illustration of a cardiac diagnostic/monitoring system operatively connected to a patient via a twelve lead system in accordance with an embodiment.

Referring to FIG. 1, a schematically represented cardiac diagnostic/monitoring system 6 is adapted measure an electrical signal generated by a patient's heart. The cardiac diagnostic/monitoring system 6 can be coupled to the patient 12 by an array of sensors or transducers. In the illustrated embodiment, the array of sensors include a right arm electrode RA; a left arm electrode LA; chest electrodes V1, V2, V3, V4, V5 and V6; a right leg electrode RL; and a left electrode leg LL for acquiring a standard twelve lead, ten-electrode electrocardiogram (ECG) signal. The twelve ECG leads include leads I, II, V1, V2, V3, V4, V5 and V6 which are acquired directly from the patient leads, and leads III, aVR, aVL and aVF which are derived using Einthoven's law. The cardiac diagnostic/monitoring system 6 comprises a processor 8 configured to generate a patient diagnosis based on the measured cardiac electrical signals as will be described in detail hereinafter.

Figure 2:
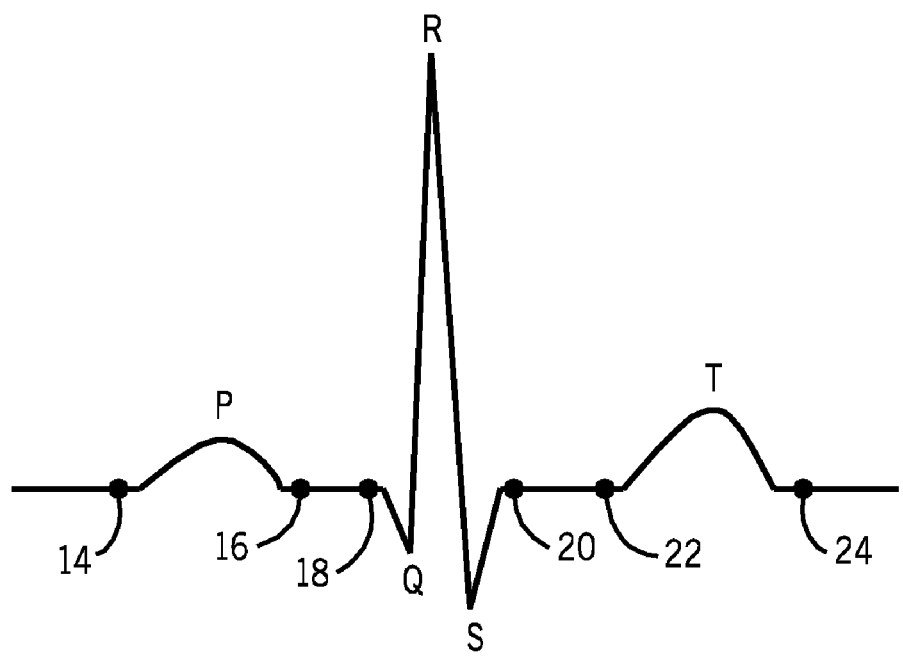
FIG. 2 is a PQRST complex of an electrocardiogram in accordance with an embodiment.

Referring to FIG. 2, an electrocardiogram (ECG) of a single heartbeat typically referred to as a PQRST complex is shown. The portion of the PQRST complex defined between reference points 14 and 16 is defined as the P-wave, and corresponds to activity in the atria. The portion of the PQRST complex defined between reference points 18 and 20 is defined as the QRS complex, and represents the electrical activation of the ventricles. The portion of the PQRST complex defined between reference points 22 and 24 is defined as the T-wave, and represents the electrical recovery or recharge phase of the ventricles. The portion of the PQRST complex defined between reference points 20 and 22 is defined as the ST segment. The portion of the PQRST complex defined between reference points 20 and 24 comprising both the ST segment and the T-wave will hereinafter be referred to as the ST-T segment.

Figure 3:
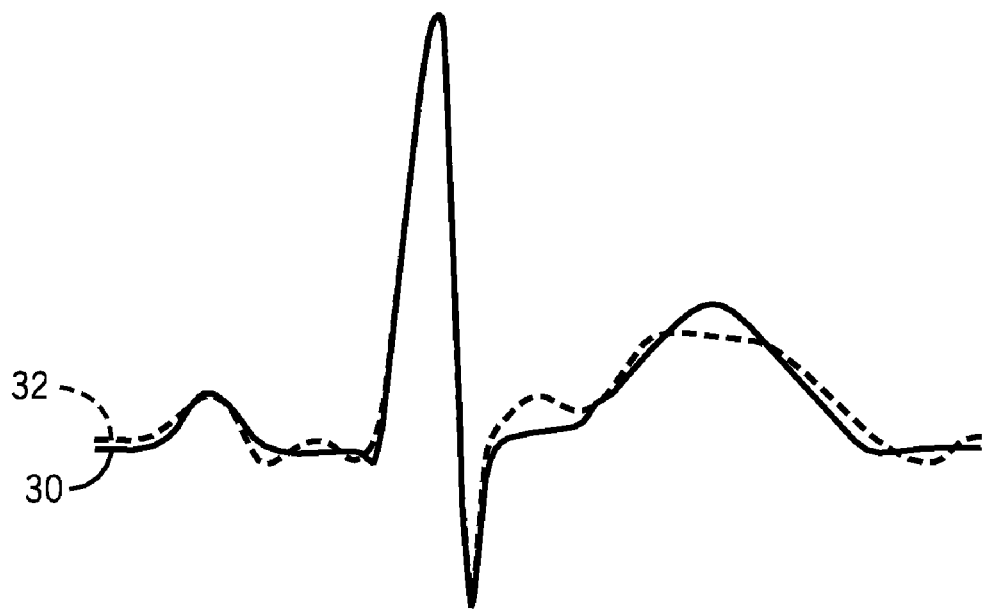
FIG. 3 shows two consecutive PQRST complexes that have been superimposed in accordance with an embodiment.

T-wave alternans (TWA) is an electrophysiological phenomenon that is evident in the ECG as an alternating pattern of ST-T segment morphologies on consecutive beats. Referring to FIG. 3, two consecutive PQRST complexes have been superimposed to illustrate TWA. More precisely, a first PQRST complex 30 illustrated with a solid line has been superimposed onto an immediately consecutive PQRST complex 32 illustrated with a dashed line.

According to one embodiment, TWA is measured as the maximum differential between the ST-T segment of the PQRST complex 30 and the ST-T segment of the PQRST complex 32. For purposes of this disclosure, the term differential refers to the difference between two or more data points and is typically measured in microvolts. As an example, if the ST segment of the PQRST complex 32 exceeds that of the PQRST complex 30 by a maximum amount of 3.0 microvolts, and the T-wave portion of the PQRST complex 30 exceeds that of the PQRST complex 32 by a maximum amount of 5.0 microvolts, the TWA measurement for the consecutive PQRST complexes 30, 32 may be defined as 5.0 microvolts. This TWA measurement can be compared with previously acquired research or test data in order to identify cardiac electrical instability.

According to another embodiment, a user can identify specific portions of the PQRST complex 30 and the PQRST complex 32 to be evaluated. According to this embodiment, TWA is measured as the maximum differential between the PQRST complex 30 and the PQRST complex 32 as measured in the identified portions of the respective complexes 30 and 32. It should be appreciated that the identified portions of the complexes 30 and 32 may comprise a specific point or a range of points to be evaluated.

The preceding method for measuring TWA is merely illustrative, and TWA may alternatively be measured in a variety of different manners. Some methods for measuring TWA are more capable of identifying cardiac electrical instability than others. In an effort to develop and validate an improved TWA measurement adapted to identify the highest percentage of patients with cardiac electrical instability, a clinical study comprising 681 patients was conducted and the method 100 (shown in FIG. 4) was validated. The clinical study will now be described in more detail.

During the course of the clinical study, it was observed that a first subset of patients with cardiac electrical instability is identifiable with a short duration high differential TWA measurement, and a second generally distinct subset of patients with cardiac electrical instability is identifiable with a long duration low differential TWA measurement. As a result of this observation, the method 100 (shown in FIG. 4) assesses cardiac electrical instability based on two distinct TWA measurements in order to identify the greatest percentage of patients with cardiac electrical instability. For purposes of this disclosure a short duration TWA (SDTWA) measurement is a TWA measurement derived from 16 or fewer consecutive heartbeats, and a long duration TWA (LDTWA) measurement is a TWA measurement derived from 64 or more consecutive heartbeats. Also for purposes of this disclosure, the term high differential should be defined to include differentials in excess of 40 microvolts, and the term low differential should be defined to include differentials below 10 microvolts. It will be appreciated by those skilled in the art that SDTWA is sometimes referred to as non-sustained TWA, and LDTWA is sometimes referred to as sustained TWA.

Support for the previously described clinical study observation can be seen from the following data. Over a three-year period, approximately 3.0% of the clinical study patients having cardiac electrical instability resulting in sudden arrhythmic death were identifiable using either short duration high differential TWA measurements or long duration low differential TWA measurements. By generally simultaneously measuring both short duration high differential and long duration low differential TWA, approximately 6.0% of the clinical study patients having cardiac electrical instability resulting in sudden arrhythmic death were identifiable. In contrast, no patients died if neither the short duration high differential TWA or long duration low differential TWA was detected. It can be seen from this data that a combined short and long duration TWA measurement identified twice as many patients with cardiac electrical instability as compared to a measurement relying on either short or long duration TWA exclusively.

Referring to FIG. 4, the method 100 will now be described in accordance with an embodiment. As shown, the method 100 comprises steps 102-107. According to one embodiment, one or more of the steps 102-107 may be performed by the processor 8 of the cardiac diagnostic/monitoring system 6 (shown in FIG. 1).

At step 102, a SDTWA measurement is obtained. At step 104, a LDTWA measurement is obtained. At step 106, a cardiac electrical instability assessment is obtained based on both the SDTWA measurement of step 102 and the LDTWA measurement of step 104. At step 107, a TWA burden analysis is performed. Having briefly described each step of the method 100, the individual steps 102-107 will now be described in more detail.

Referring to FIG. 5, step 102 of the method 100 (shown in FIG. 4) will now be described in accordance with an embodiment. As shown, step 102 comprises steps 110-116. According to one embodiment, one or more of the steps 110-116 may be performed by the processor 8 of the cardiac diagnostic/monitoring system 6 (shown in FIG. 1). It should be appreciated that the steps 110-116 need not necessarily be performed in the order shown.

At step 110, PQRST complex data pertaining to a plurality of sequential heartbeats is bifurcated into even beat data and odd beat data. At step 112, a predetermined portion of the even beat data is extracted and averaged to produce an even beat average. According to one embodiment, at step 112, the ST-T segments are extracted from the even beat data and are thereafter averaged. At step 114, a predetermined portion of the odd beat data is extracted and averaged to produce an odd beat average. According to one embodiment, at step 114, the ST-T segments are extracted from the odd beat data and are thereafter averaged. At step 116, the even beat averages are compared with the odd beat averages. According to one embodiment, the step 116 comparison includes identifying the maximum difference between the even beat averages and the odd beat averages.

Figure 6:
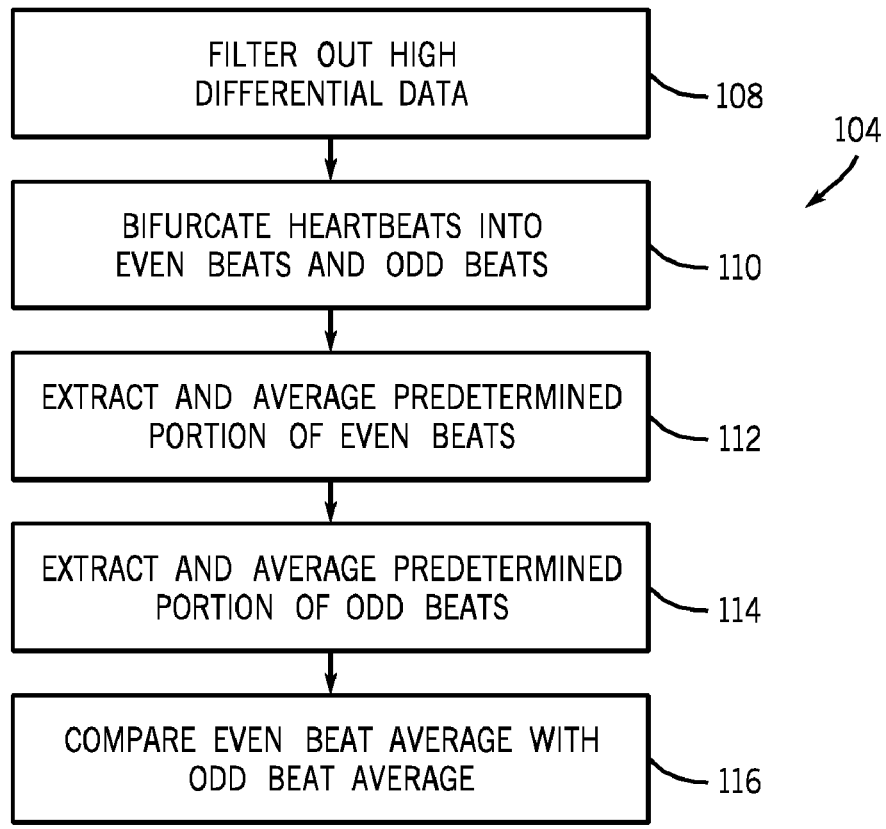
FIG. 6 is a flow chart in accordance with an embodiment.

Referring to FIG. 6, step 104 of the method 100 (shown in FIG. 4) will now be described in accordance with an embodiment. As shown, step 104 comprises steps 108-116. According to one embodiment, one or more of the steps 108-116 may be performed by the processor 8 of the cardiac diagnostic/monitoring system 6 (shown in FIG. 1). It should be appreciated that the steps 108-116 need not necessarily be performed in the order shown.

Steps 110-116 were previously described with respect to FIG. 5 and will therefore not be described again. Step 108 is an optional step that may be implemented to filter out or otherwise eliminate high differential data from the LDTWA measurement. The filtration may be performed in a variety of known ways such as with a low-pass filter or with an algorithm adapted to digitally eliminate any data exceeding a predefined high differential limit before the LDTWA measurement is performed. The process of filtering out the high differential data from the LDTWA measurement prevents this data from introducing imprecision into the LDTWA measurement. In other words, if the high differential data is not filtered, it could skew the resultant LDTWA measurement and yield an imprecise or misleading result.

Figure 7:
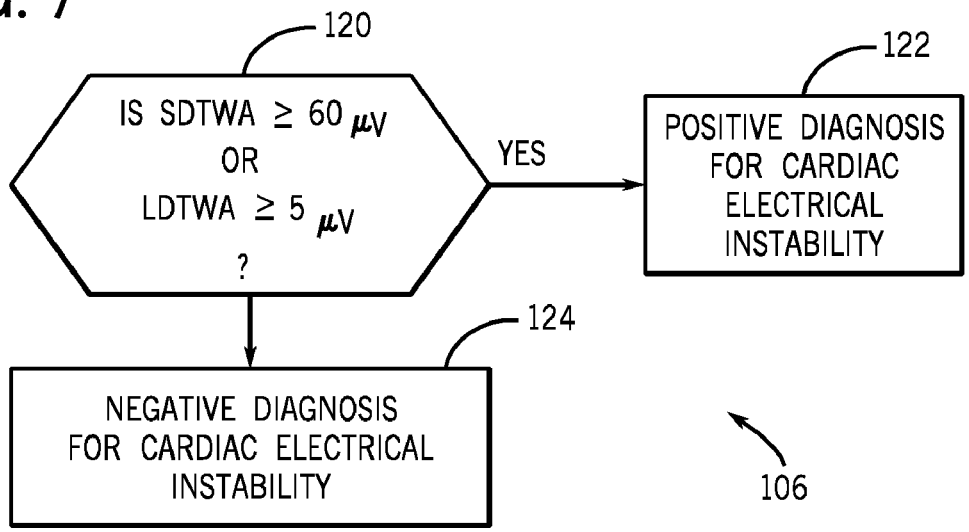
FIG. 7 is a flow chart in accordance with an embodiment.

Referring to FIG. 7, step 106 of the method 100 (shown in FIG. 4) will now be described in accordance with an embodiment. As shown, step 106 comprises steps 120-124. According to one embodiment, one or more of the steps 120-124 may be performed by the processor 8 of the cardiac diagnostic/monitoring system 6 (shown in FIG. 1).

At step 120, it is determined if the SDTWA measurement obtained at step 102 (shown in FIG. 5) exceeds a predetermined high differential limit. According to one embodiment, step 120 determines if the SDTWA measurement exceeds 60 microvolts. At step 120, it is also determined if the LDTWA measurement obtained at step 104 (shown in FIG. 6) exceeds a low differential limit. According to one embodiment, step 120 determines if the LDTWA measurement exceeds 5 microvolts. If, at step 120, the SDTWA measurement exceeds the high differential limit or the LDTWA measurement exceeds the low differential limit, the algorithm proceeds to step 122 at which the patient is positively diagnosed for cardiac electrical instability. If, at step 120, the SDTWA measurement does not exceed the high differential limit and the LDTWA measurement does not exceed the low differential limit, the algorithm proceeds to step 124 at which the patient is negatively diagnosed for cardiac electrical instability.

Referring again to FIG. 4, step 107 of the method 100 will now be described in more detail. The TWA burden analysis of step 107 is optional and is adapted to provide a quantitative assessment along with each cardiac electrical instability diagnosis. In other words, the TWA burden analysis provides a degree of concern assessment that is intended to convey the seriousness of a given cardiac electrical instability diagnosis.

According to one embodiment, the TWA burden analysis of step 107 may be performed by calculating the number of times the SDTWA measurement of step 102 exceeds a first predefined threshold (e.g., 60 microvolts); and the number of times the LDTWA measurement of step 104 exceeds a second predefined threshold (e.g., 5 microvolts). The following will provide an example illustrating this embodiment. For purposes of this illustrative example, assume a first patient exceeds a 60 microvolt threshold three times during a SDTWA measurement and exceeds a 5 microvolt threshold two times during a LDTWA measurement. Also for purposes of this illustrative example, assume that a second patient does not exceeds the 60 microvolt threshold during a SDTWA measurement and exceeds the 5 microvolt threshold one time during a LDTWA measurement. Both patients would receive a positive diagnosis for cardiac electrical instability at step 106 described in detail hereinabove with FIG. 7; however, the first patient would also receive a TWA burden analysis of five indicating a greater degree of concern as compared to the second patient having a TWA burden analysis of one.

According to another embodiment, the TWA burden analysis of step 107 may be performed by measuring the duration or amount of time during which the SDTWA measurement of step 102 exceeds a first predefined threshold (e.g., 60 microvolts); and the amount of time during which the LDTWA measurement of step 104 exceeds a second predefined threshold (e.g., 5 microvolts). The following will provide an example illustrating this embodiment. For purposes of this illustrative example, assume a first patient exceeds a 60 microvolt threshold for a period of three seconds during a SDTWA measurement and exceeds a 5 microvolt threshold for a period of two seconds during a LDTWA measurement. Also for purposes of this illustrative example, assume that a second patient does not exceeds the 60 microvolt threshold during a SDTWA measurement and exceeds the 5 microvolt threshold for a period of one second during a LDTWA measurement. Both patients would receive a positive diagnosis for cardiac electrical instability at step 106 described in detail hereinabove with FIG. 7; however, the first patient would also receive a TWA burden analysis of five seconds indicating a greater degree of concern as compared to the second patient having a TWA burden analysis of one second.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method comprising:
    obtaining a short duration T-wave alternans (SDTWA) measurement using a processor;
    obtaining a long duration T-wave alternans (LDTWA) measurement using a processor;
    comparing the SDTWA measurement to a high differential limit;
    comparing the LDTWA measurement to a low differential limit that is different from the high differential limit; and
    calculating a cardiac electrical instability assessment using a processor based on the results of the comparisons of both the SDTWA measurement to the high differential limit and the LDTWA measurement to the low differential limit.

2. The method of claim 1, wherein said obtaining a SDTWA measurement comprises obtaining a SDTWA measurement based on data acquired from no more than 16 consecutive heartbeats.

3. The method of claim 1, wherein said obtaining a LDTWA measurement comprises obtaining a LDTWA measurement based on data acquired from at least 64 consecutive heartbeats.

4. The method of claim 1, wherein said step of obtaining a LDTWA measurement comprises eliminating high differential data from the LDTWA measurement.

5. The method of claim 1, wherein said obtaining a SDTWA measurement and said obtaining a LDTWA measurement each comprise bifurcating data derived from a plurality of sequential heartbeats into even beat data and odd beat data.

6. The method of claim 5, wherein said obtaining a SDTWA measurement and said obtaining a LDTWA measurement each comprise extracting a ST-T segment of the even beat data and the odd beat data.

7. The method of claim 6, wherein said obtaining a SDTWA measurement and said obtaining a LDTWA measurement each comprise establishing an even ST-T segment average based on the even beat data and an odd ST-T segment average based on the odd beat data.

8. The method of claim 7, wherein said obtaining a SDTWA measurement and said obtaining a LDTWA measurement each comprise comparing the even ST-T segment average with the odd ST-T segment average.

9. The method of claim 4, wherein said eliminating high differential data from the LTDWA comprises eliminating differentials in excess of 40 microvolts from the LTDWA.

10. The method of claim 1, wherein said obtaining a cardiac electrical instability assessment comprises diagnosing cardiac electrical instability if the SDTWA measurement exceeds the high differential limit or if the LDTWA measurement exceeds the low differential limit.

11. The method of claim 10, wherein said obtaining a cardiac electrical instability assessment comprises diagnosing cardiac electrical instability if the SDTWA measurement exceeds the high differential limit of 60 microvolts or if the LDTWA measurement exceeds the low differential limit of 5 microvolts.

12. The method of claim 1, further comprising performing a TWA burden analysis in order to obtain a degree of concern assessment.

13. A method comprising:
- obtaining a short duration T-wave alternans (SDTWA) measurement using a processor;
- obtaining a long duration T-wave alternans (LDTWA) measurement using a processor, said obtaining the LDTWA measurement comprising eliminating high differential data from the LDTWA measurement;
- comparing the SDTWA measurement to a high differential limit;
- comparing the LDRWA measurement to a low differential limit that is different from the high differential limit;
- diagnosing cardiac electrical instability if the SDTWA measurement exceeds the high differential limit or if the LDTWA measurement exceeds the low differential limit; and
- performing a TWA burden analysis using a processor in order to obtain a degree of concern assessment.

14. The method of claim 13, wherein said obtaining a SDTWA measurement and said obtaining a LDTWA measurement each comprise bifurcating data derived from a plurality of sequential heartbeats into even beat data and odd beat data.

15. The method of claim 14, wherein said obtaining a SDTWA measurement and said obtaining a LDTWA measurement each comprise extracting a ST-T segment of the even beat data and the odd beat data.

16. The method of claim 15, wherein said obtaining a SDTWA measurement and said obtaining a LDTWA measurement each comprise establishing an even ST-T segment average based on the even beat data and an odd ST-T segment average based on the odd beat data.

17. The method of claim 16, wherein said obtaining a SDTWA measurement and said obtaining a LDTWA measurement each comprise comparing the even ST-T segment average with the odd ST-T segment average.

18. A system comprising:
- a plurality of sensors configured to record an ECG; and
- a processor operatively connected to the plurality of sensors, said processor configured to:
  - obtain a short duration T-wave alternans (SDTWA) measurement based on the recorded ECG;
  - obtain a long duration T-wave alternans (LDTWA) measurement based on the recorded ECG;
  - compare the SDTWA measurement to a high differential limit;
  - compare the LDTWA measurement to a low differential limit that is different from the high differential limit; and
  - generate a cardiac electrical instability assessment based on the results of the comparisons of both the SDTWA measurement to the high differential limit and the LDTWA measurement to the low differential limit.

19. The system of claim 18, wherein said processor is configured to positively diagnose cardiac electrical instability if the SDTWA measurement exceeds the high differential limit or if the LDTWA measurement exceeds the low differential limit.

20. The system of claim 19, wherein said processor is configured to positively diagnose cardiac electrical instability if the SDTWA measurement exceeds 60 microvolts or if the LDTWA measurement exceeds 5 microvolts.

21. The system of claim 18, wherein said processor is configured to perform a TWA burden analysis in order to obtain a degree of concern assessment.

* * * * *

UNITED STATES PATENT AND TRADEMARK OFFICE
CERTIFICATE OF CORRECTION

PATENT NO. : 8,060,192 B2
APPLICATION NO. : 12/332095
DATED : November 15, 2011
INVENTOR(S) : Rowlandson et al.

Page 1 of 1

It is certified that error appears in the above-identified patent and that said Letters Patent is hereby corrected as shown below:

On the Title Page, in Item (56), in Column 2, Line 17,
above "* cited by examiner", insert -- OTHER PUBLICATIONS
PowerPoint presentation entitled "Progress Report – T Wave Alternans", MORTARA INSTRUMENT, Second Annual Mortara ECG Seminar, St. Thomas, Feb., 2007. --.

Signed and Sealed this
Eleventh Day of September, 2012

David J. Kappos
*Director of the United States Patent and Trademark Office*